(12) United States Patent
Pobiel

(10) Patent No.: US 11,806,532 B2
(45) Date of Patent: Nov. 7, 2023

(54) IMPLANTABLE LEAD WITH ASYMMETRIC FIDUCIAL MARKER

(71) Applicant: Heraeus Medical Components LLC, St. Paul, MN (US)

(72) Inventor: Benjamin Pobiel, St. Paul, MN (US)

(73) Assignee: Heraeus Medical Components LLC, St. Paul, MN (US)

(*) Notice: Subject to any disclaimer, the term of this patent is extended or adjusted under 35 U.S.C. 154(b) by 307 days.

(21) Appl. No.: 16/952,680

(22) Filed: Nov. 19, 2020

(65) Prior Publication Data

US 2021/0154473 A1 May 27, 2021

Related U.S. Application Data

(60) Provisional application No. 62/940,382, filed on Nov. 26, 2019.

(51) Int. Cl.
*A61N 1/36* (2006.01)
*A61B 90/00* (2016.01)
*A61N 1/05* (2006.01)

(52) U.S. Cl.
CPC .......... *A61N 1/3605* (2013.01); *A61B 90/39* (2016.02); *A61N 1/05* (2013.01); *A61B 2090/363* (2016.02); *A61B 2090/3966* (2016.02); *A61B 2090/3983* (2016.02)

(58) Field of Classification Search
None
See application file for complete search history.

(56) References Cited

U.S. PATENT DOCUMENTS

| | | | | |
|---|---|---|---|---|
| 5,824,042 A | * | 10/1998 | Lombardi | A61B 90/39 623/1.13 |
| 2013/0046369 A1 | | 2/2013 | Eggen et al. | |
| 2013/0325091 A1 | * | 12/2013 | Pianca | A61N 1/056 607/116 |
| 2015/0039068 A1 | * | 2/2015 | Romero | A61N 1/0556 607/116 |
| 2016/0361535 A1 | | 12/2016 | Perryman et al. | |
| 2018/0104472 A1 | * | 4/2018 | Govea | A61N 1/05 |

FOREIGN PATENT DOCUMENTS

| | | |
|---|---|---|
| WO | 2019/060058 | 3/2019 |
| WO | 2019/084182 | 5/2019 |
| WO | 2019/148094 | 8/2019 |

* cited by examiner

*Primary Examiner* — Erica S Lee
*Assistant Examiner* — Elizabeth K So
(74) *Attorney, Agent, or Firm* — Dicke, Billig & Czaja, PLLC

(57) ABSTRACT

One aspect provides a fiducial marker for use with an implantable lead, the fiducial marker having a structure extending along and about a longitudinal axis, the structure having an asymmetrical shape about the longitudinal axis when viewed in any radial direction from the longitudinal axis so as to provide a unique radioscopic silhouette in any radial direction.

17 Claims, 6 Drawing Sheets

IMPLANTABLE LEAD WITH ASYMMETRIC FIDUCIAL MARKER

CROSS-REFERENCE TO RELATED APPLICATION

This Utility patent application claims priority to U.S. Application No. 62/940,382 filed on Nov. 26, 2019, which is incorporated herein by reference.

TECHNICAL FIELD

This disclosure relates to sensing and/or stimulating leads for use with implantable medical devices, such as cardiac pacemakers, cardiac defibrillators, and neurostimulators, for example, and in particular, to a fiducial marker for use with such leads to enable desired positioning of the leads within a biological application (e.g., when implanted within the body of a mammal or human).

BACKGROUND

In some cases, sensing/stimulating leads include a number of electrodes disposed about a circumference of a distal end, where each electrode is individually controllable to provide discrete, directional, and localized sensing and/or stimulation of adjacent tissue. To avoid monitoring or stimulating unintended areas, the distal end of the lead must be properly oriented at a desired position within a body. In some cases, to assist with such positioning, a fiducial marker (or markers) is attached at the distal end at a known location with respect to the electrodes, where the fiducial marker provides a fluoroscopic image that assists a physician in determining the orientation of the lead within the body. However, from fluoroscopic images provided by known fiducial markers, the orientation of the distal end of the lead may not always be apparent. For these and other reasons there is a need for the embodiments of the present disclosure.

SUMMARY

A fiducial marker for use with an implantable lead, the fiducial marker having a structure extending along and about a longitudinal axis, the structure having an asymmetrical shape about the longitudinal axis when viewed in any radial direction from the longitudinal axis so as to provide a unique radioscopic silhouette in any radial direction.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Figure 1:
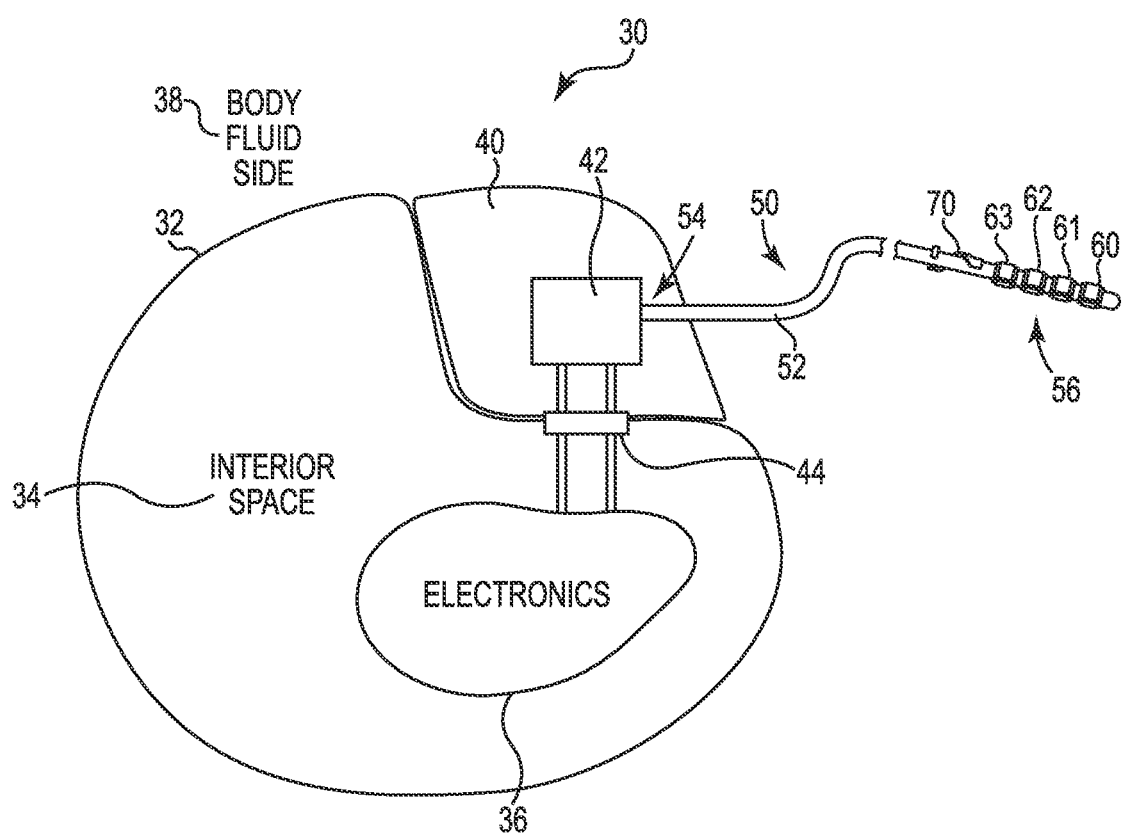
FIG. 1 is a block and schematic diagram generally illustrating an implantable medical device including a lead having a fiducial marker, according to one example.

FIG. 1 is a block and schematic diagram generally illustrating an implantable medical device 30, such as a neurostimulator, according to one example. Implantable medical device 30 includes a hermetically sealed metal case or housing 32, typically formed of titanium, which defines a hermetically sealed interior space 34 in which device electronics 36 are disposed and protected from fluids of the body fluid side 38 external to housing 32. A header 40 attaches to housing 32 and includes a connector block 42 which typically includes one or more sockets for connecting to one or more sensing and/or stimulating leads, such as sensing and/or stimulating lead 50, that extend between implantable medical device 30 and desired regions of the body, such as the human heart and brain, for example. A feedthrough device 44 establishes electrical pathways or connections through housing 32 to header 40 that maintain the integrity of hermetically sealed interior space 34 and provide electrical connection of lead 50, via connector block 42, to internal device electronics 36.

In one example, lead 50 includes a lead body 52 having a proximal end 54 connected to connector block 42 and a distal end 56 to be placed proximate to desired tissue within a biologic body. In one example, distal end 56 includes a number of electrodes 60-63, where each electrode is individually controllable by electronics 36 via conductors (see FIG. 2) disposed within lead body 52 and connected between connector block 42 and electrodes 60-63. In one example, as will be described in greater detail below, each of the electrodes 60-63 is segmented to provide a number of segmented electrodes (see FIG. 2) about a circumference of distal end 56 so that lead 50 is able to provide directional stimulation/sensing. In one example, distal end 56 further includes a fiducial marker 70, in accordance with the present disclosure, which, via a fluoroscopic image thereof, provides indication of an angular orientation of distal end 56 when disposed within a body. In one example, as will be described in greater detail below, fiducial marker 70, in accordance with the present disclosure, has a shape which, when viewed in any radial direction from a longitudinal axis of lead body 52, is asymmetrical about the longitudinal axis. As a result, fiducial marker 70 provides a unique fluoroscopic silhouette in any radial directional and, thereby, provides clear indication of an angular orientation of distal end 56 within a biologic body when viewed from any radial direction.

Figure 2:
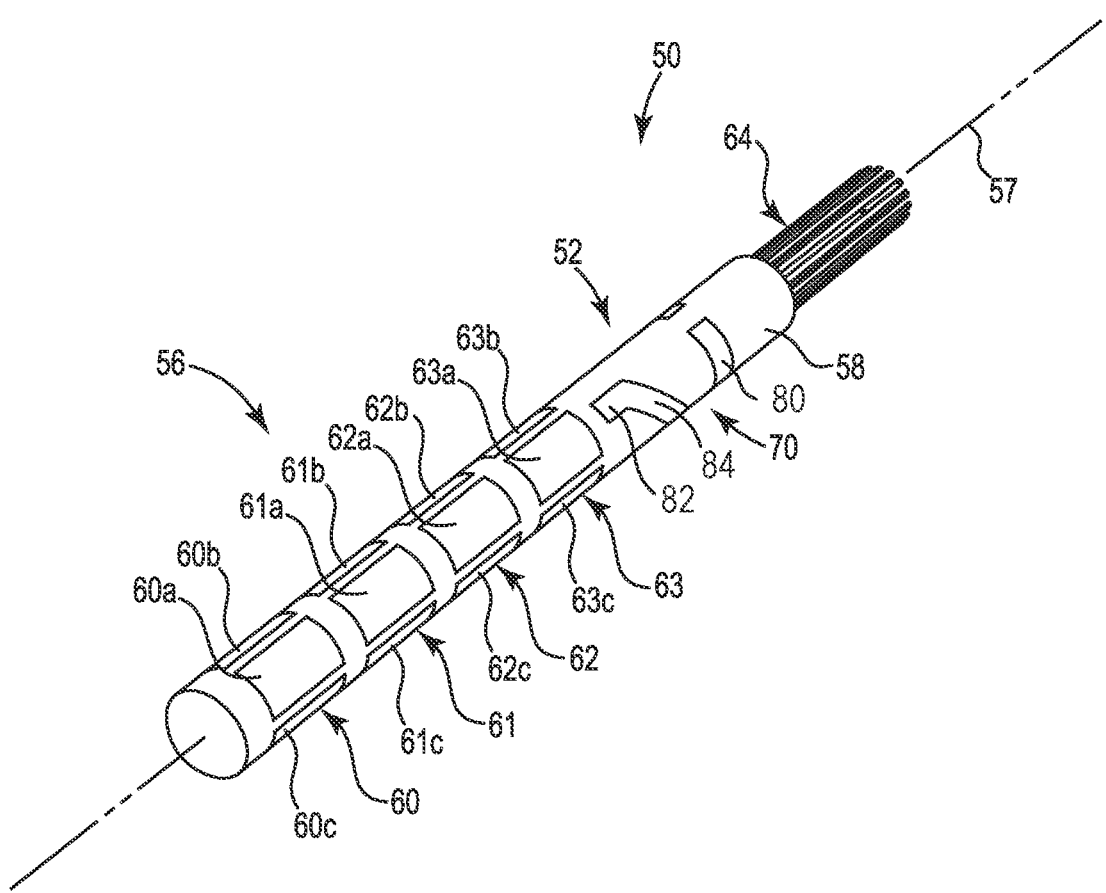
FIG. 2 is a perspective view generally illustrating a portion of an implantable lead including a fiducial marker, according to one example.

FIG. 2 is a perspective view generally illustrating a portion of lead 50, including distal end 56. In one example, as illustrated, electrodes 60-63 and fiducial marker 70 are laterally spaced apart from one another along a longitudinal axis 57 of lead 50, and are embedded within a molded or reflowed insulating material 58. In one example, fiducial marker 70 is fully embedded within molded or reflowed insulating material 58, and in another example, fiducial marker 70 extends radially slightly out of molded or reflowed insulating material 58. In one example, fiducial marker 70 is made of the same material as electrodes 60-63, but in other examples is of any material that meets the appropriate radiopaque, design, and biocompatibility requirements of the particular application.

In one example, as illustrated, each electrode 60-63 is segmented into three electrode segments, with electrode 60 including first, second, and third electrode segments 60a, 60b, and 60c; electrode 61 including first, second, and third electrode segments 61a, 61b, and 61c; electrode 62 including first, second, and third electrode segments 62a, 62b, and 62c; and electrode 63 including first, second, and third electrode segments 63a, 63b, and 63c. In one example, electrode segments a-c of each of the electrodes 60-63 are circumferentially spaced from one another and extend about a segment of the circumference of leady body 52 (e.g., 110-degrees).

Lead 50 further includes a number of conductors 64 (also referred to herein as a conductor bundle 64) embedded within and extending coextensively with insulating material 58 along longitudinal axis 57 of lead 50 from proximal end 54 to electrodes 60-63 at distal end 56. In one example, conductor bundler 64 includes a separate conductor for each of the electrodes segments a-c of each of the electrodes 60-63, with each conductor being internally electrically connected to its respective electrode segment a-c of electrodes 60-63 at distal end 56. Similarly, but not illustrated, in one example, each conductor of conductor bundle 64 may be electrically connected to a connector at proximal end 54 for electrical connection to electronics 36 via connector block 42.

In one example, lead 50 has a round cross-section. Depending on the particular application (e.g., neurological and myocardial mapping/ablation, and neuromodulation and stimulation), a diameter of lead body 52 may be of any number of sizes. In one example, lead 50 comprises a 1.3 mm outer diameter lead. In another example, lead 50 comprises a 0.8 mm outer diameter lead. In other examples, depending on the on the particular application, lead 50 may have cross-sectional shapes other than round or circular (e.g., an elliptical shape).

Insulating molded and/or reflowed material 58 electrically insulates electrodes 60-63, fiducial marker 70, and conductor bundle 64 from one another (other than the electrical connection between each conductor of conductor bundle 64 and its respective electrode segment a-c of electrodes 60-63). In one example, molded or reflowed insulating material 58 comprises a biocompatible and biostable material which may be selected based on the particular application of lead 50. In examples, the insulator may be silicone, polyurethane, polyethylene, polyamide, polyvinylchloride, PTFT, EFTE, or other suitable material. Alloys or blends of these materials may also be formulated to control the flexibility or stiffness of lead 50.

Conductor bundle 64 may comprise solid wires, drawn-filled-tube (DFT), hypotube conductors, drawn-brazed-strand (DBS), stranded wires or cables, ribbon conductors or other suitable conductor forms. The composition of the conductors of conductor bundle 64 may include aluminum, stainless steel, platinum, gold, silver, copper, vanadium, alloys, or any suitable conductive materials or metals. In examples, the conductors of conductor bundle 64 may extend along lead body 52 in parallel with longitudinal axis 57 or be spirally or helically wound about longitudinal axis 57, such as about a central lumen (if included), or about a center of lead body 52. In one example, the conductors of conductor bundle 64 are electrically insulated from one another and from other components of lead 50, as well as from the exterior surface of lead 50, by molded or reflowed insulating material 58. In other examples, each conductor of conductor bundle 64 may be individually insulated or coated with an insulating material prior to application of molded or reflowed insulating material 58. As described above, conductors of conductor bundle 64 transmit electrical signals between electronics 36 and respective ones of the electrode segments a-c of electrodes 60-63.

In examples, electrodes 60-63 may be made of a conductive material such as platinum, gold, silver, platinum-iridium, stainless steel, or any suitable conductive materials, metals, and alloys. A size of electrodes 60-63, and segmented electrodes a-c of electrodes 60-63 may be selected based on a particular application.

Although illustrated as including four electrodes, 60-63, with each electrode being segmented to form three electrode segments a-c, it is noted that different numbers of electrodes and electrode segments may be employed in other examples. Similarly, a number of conductors in conductor bundle 64 may vary between examples.

In one example, as illustrated, fiducial marker 70 is disposed at distal end 56 at a known fixed position relative to electrodes 60-63 and has a shape different from that of electrodes 60-63. Based on the known position and shape of fiducial marker 70, fluoroscopic images of fiducial marker 70 during implantation of lead 50 within a biologic body enable a practitioner to implant distal end 56 at a desired location and with a desired orientation so that electrodes 60-63 stimulate and/or monitor the proper target tissue or area within the biologic body, and thereby enable proper use of the directional nature of electrodes 60-63.

As will be described in greater detail below, according to the present disclosure, fiducial marker 70 has a shape that provides a unique fluoroscopic image or silhouette when viewed in any radial direction from longitudinal axis 57. As a result, the angular position of distal end 56 and, thus, an angular position of electrodes 60-63 can be readily determined from fluoroscopic images. In contrast, as will be described in greater detail below, known fiducial markers have shapes which produce a similar fluoroscopic silhouettes in different radial directions (such as radial directions which are 180-degrees apart, for example), such that an angular position of the associated implantable lead may not be accurately ascertainable from such fluoroscopic images.

In one example, as illustrated, fiducial marker 70 is disposed at distal end 56 adjacent to the proximal-most electrode, in this case, adjacent to electrode 63. In one example, surfaces of fiducial marker 70 are flush with the circumferential surface of lead 50 formed by molded or reflowed insulating material 58, similar to that of electrodes 60-63.

Figure 3A:
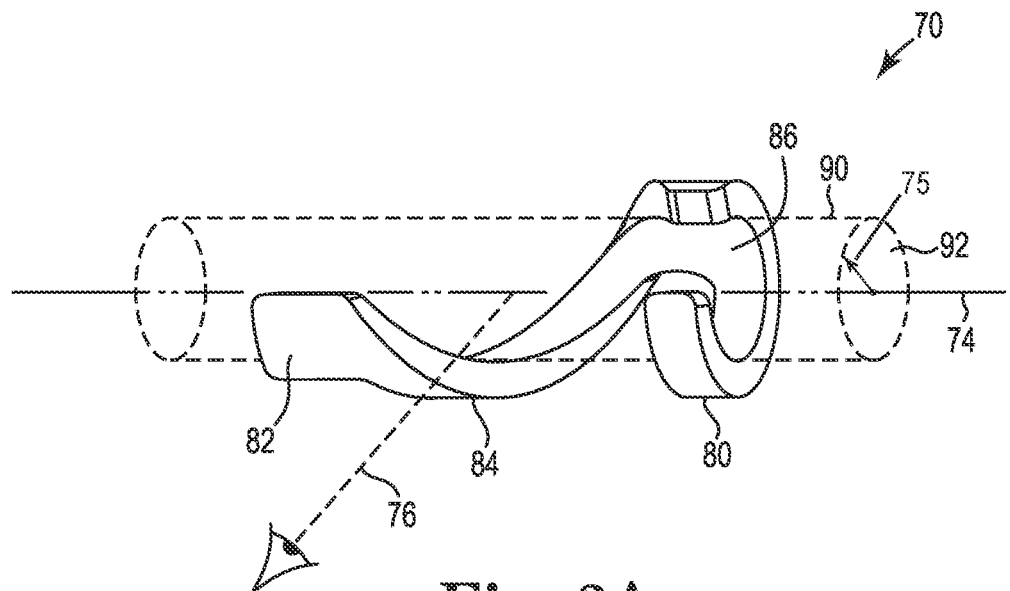
FIG. 3A is a perspective view generally illustrating a fiducial marker, according to one example.
Figure 3B:
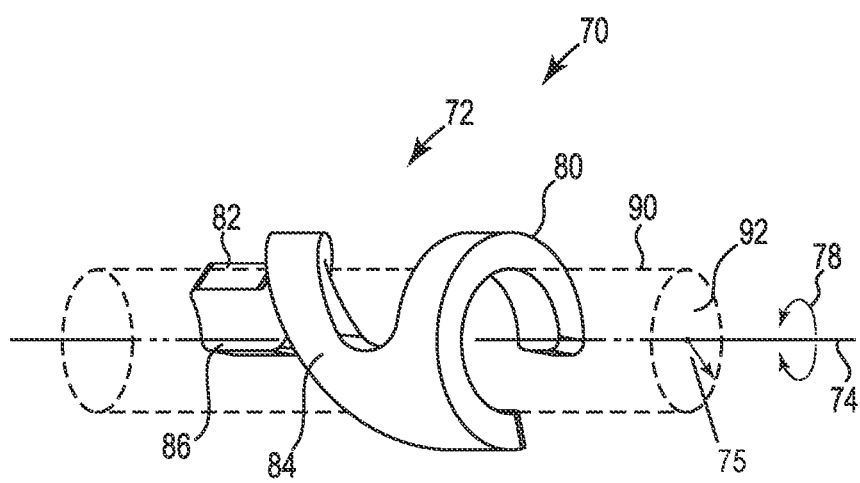
FIG. 3B is a perspective view generally illustrating a fiducial marker, according to one example.

FIGS. 3a and 3b are perspective views illustrating fiducial marker 70 of FIG. 2, according to one example. In one example, fiducial marker 70 has a structure 72 extending along and disposed about a longitudinal axis 74. According to the present disclosure, structure 72 has an asymmetrical shape about longitudinal axis 74 and a unique silhouette when viewed any radial direction from longitudinal axis 74, such as illustrated by radial arrow 75. As a result, when viewed from a given radial direction, such as radial direction 76, structure 72 will provide a unique silhouette at each angular position as fiducial marker 70 is rotated about longitudinal axis 74, as indicated by rotational arrows 78, and thereby provide a unique fluoroscopic/radiographic silhouette regardless of the angular position of fiducial marker 70 (see FIGS. 5A-5C below).

In one example, as illustrated, structure 72 of fiducial marker 70 includes a proximal portion 80, a distal portion 82, and a central portion 84 extending there between. In one example, proximal portion 80 comprises a band-shaped element extending a circular fashion (e.g., semi-circularly) about longitudinal axis 74, distal portion 82 comprises a tab extending generally parallel to longitudinal axis 74, and central portion 84 comprises a helically-shaped element extending at least semi-helically about longitudinal axis 74. In one example, as illustrated, an inner surface 86 of proximal, distal, and central portions 80, 82, and 84 of structure 72 defines an elongated channel 90 (illustrated by dashed lines) extending about and along longitudinal axis 74 which is to receive an elongated portion of lead 50, such as conductor bundle 64 (see FIG. 4). As such, in one example, elongated channel 90 has a cross-sectional shape 92 matching a cross-sectional shape of the elongated portion of lead 50 it is to receive. In example, as illustrated, elongated channel 90 is cylindrical and has a circular cross-section 92. In other examples, the cross-sectional shape 92 may be any number of shapes other than circular, such as elliptical, for example. Furthermore, although illustrated herein primarily as having a helical or semi-helical shape, the fiducial marker may have any suitable shape that provides an asymmetrical shape about the longitudinal axis when viewed in any radial direction.

Figure 4:
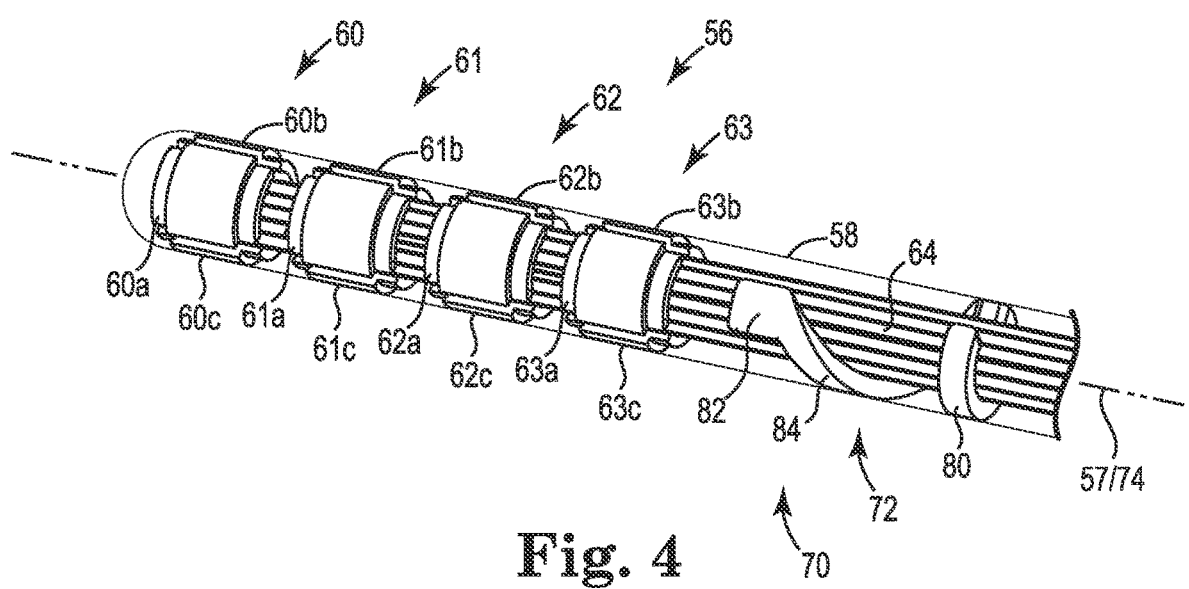
FIG. 4 is a perspective view of a distal end of an implantable lead including a fiducial marker, according to one example.

FIG. 4 is a perspective view of distal end 56 of lead 50 of FIG. 2, according to one example, where molded or reflowed insulating material 58 is shown as being transparent for clarity. As illustrated, fiducial marker 70 receives conductor bundle 64 via channel 90, with the inner surface 86 of fiducial marker 70 at least partially circumscribing the circumference of conductor bundle 64, such that longitudinal axis 74 of fiducial marker 70 coincides with the longitudinal axis 57 of lead 50. In examples, each of the conductors of conductor bundle 64 are individually insulated such that inner surface 86 may be in contact with the insulating material coating the conductors of conductor bundle 64. In other examples, the conductors of conductor bundle 64 may uncoated conductors. Accordingly, in one example, inner surface 86 of fiducial marker 70 may be coated with an insulating material so as to electrically insulate fiducial maker 70 and conductor bundler 64 from one another.

In one example, distal portion 82 comprises a linear tab extending substantially parallel to longitudinal axis 57. In one example, fiducial marker 70 is positioned on lead 50 such that linear tab 82 is positioned proximate to a known row of segmented electrodes, such as the row of electrodes comprising segment electrodes 60a, 61a, 62a, and 63a (where such row of electrodes may sometimes referred to as a "channel"). As such, in one example, tab 82 provides a known reference point which indicates a known fixed position of fiducial marker 70 relative to electrodes 60-63. As described above, by knowing a fixed position of fiducial marker 70 relative to electrodes 60-63 and by structure 72 being asymmetric about longitudinal axis 57/74 in any radial direction, fiducial marker 70 provides a unique fluoroscopic (radioscopic) silhouette from any radial direction of longitudinal axis 57/74 so that the angular position of lead 50 is readily ascertainable from an image taken along any radius.

Figure 5A:
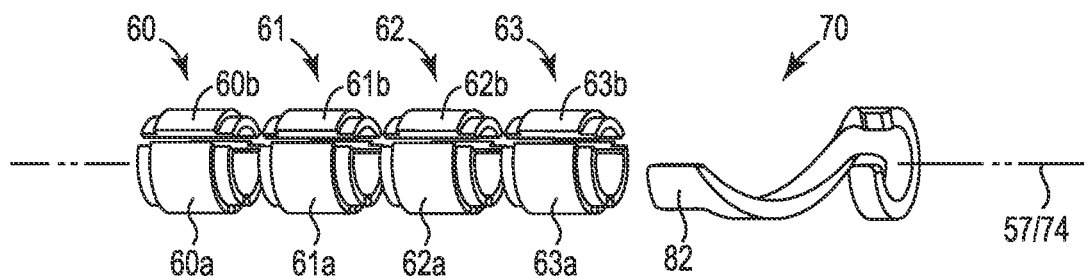
FIG. 5A is a perspective view of portions of a distal end of an implantable lead including a fiducial marker, according to one example.
Figure 5B:
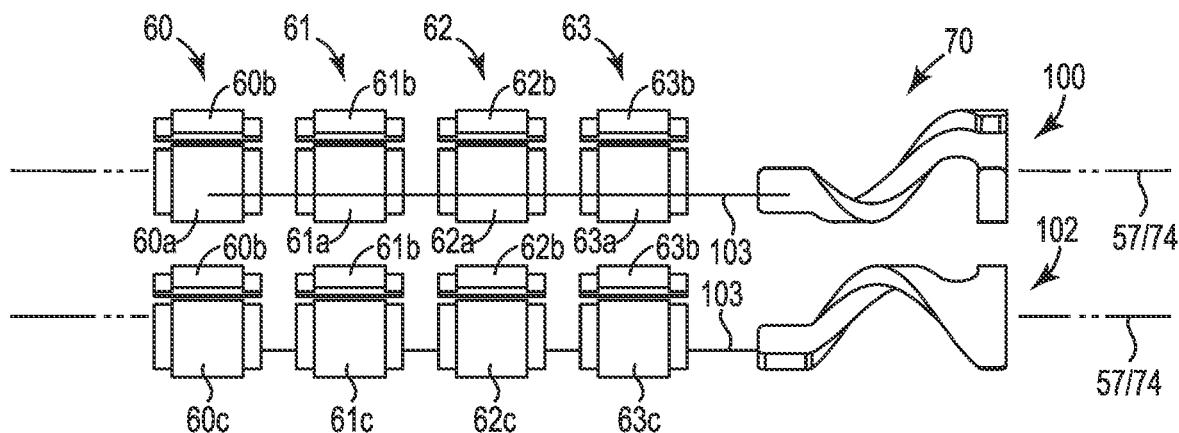
FIG. 5B is a radial view of the distal end of the implantable lead of FIG. 5A with the implantable lead at first and second angular positions, according to one example.
Figure 5C:
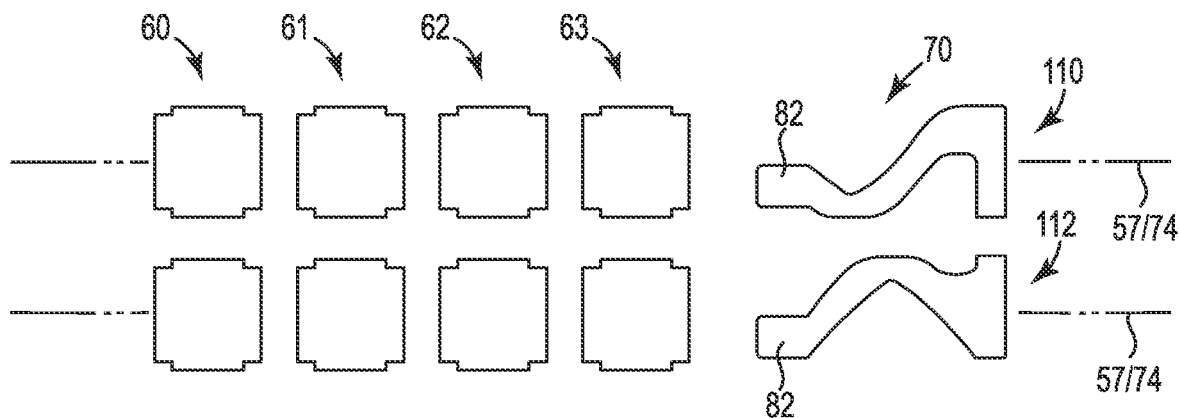
FIG. 5C generally illustrates radiographic images of the distal end of the implantable lead of FIG. 5A with the implantable lead at first and second angular positions.

FIGS. 5A-5C illustrate the visible and radiographic appearance of fiducial marker 70 of FIGS. 2-4 above when installed on lead 50, in accordance with the present disclosure. It is noted that lead body 52 is not shown in any of the FIGS. 5A-5C for clarity of illustration. FIG. 5A is a perspective view, similar to that illustrated by FIG. 4. FIG. 5B includes a first view 100 of distal end 56 when viewed from a given radial direction, such as radial direction 76 of FIG. 3A, where distal end 56 is at a first angular orientation. FIG. 5B further includes a second view 102 from the same radial direction, except that distal end 56 is shown as having been rotated about longitudinal axis 57/74 by 180 degrees. In FIG. 5B, the line 103 is intended to illustrate that fiducial marker 70 is disposed proximate to channel "a" (i.e., electrode segments 60a-63a) and faces the viewer in view 100, and faces away from the view in view 102.

FIG. 5C includes views 110 and 112 which represent radiographic images of distal end 56 respectively corresponding to views 110 and 102 of FIG. 5B. As illustrated, the angular position of distal end 56 is clear from the radiographic images represented at 110 and 112 as the radiographic silhouette of fiducial marker 70 in image 110 is clearly unique from the silhouette of fiducial marker 70 in image 112 due to the asymmetric shape of fiducial marker 70 about longitudinal axis 57/74. While views 110 and 112 illustrate the radiographic silhouettes of only two angular positions of distal end 56, as described above, the radiographic silhouette of fiducial marker 70 will be unique at each angular position of distal end 56. By providing a unique radiographic silhouette at each angular position of proximal end 56, fiducial marker 70 enables a practitioner to readily ascertain the angular orientation of proximal end 56 from a radiographic image taken in any radial direction from longitudinal axis 57.

Figure 6A:
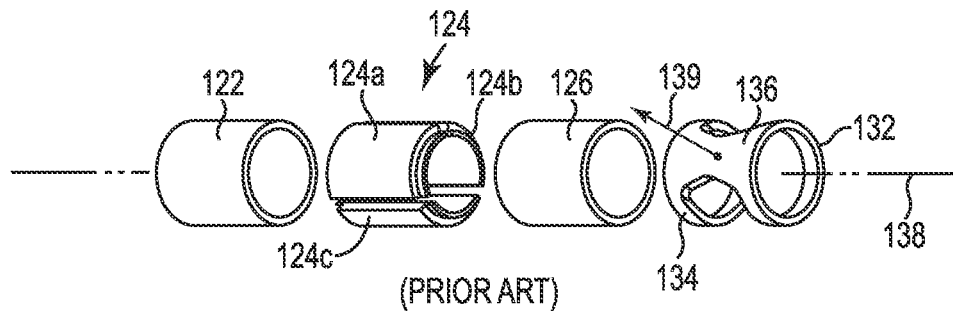
FIG. 6A is a perspective view of portions of a distal end of a known implantable lead including a known fiducial marker.
Figure 6B:
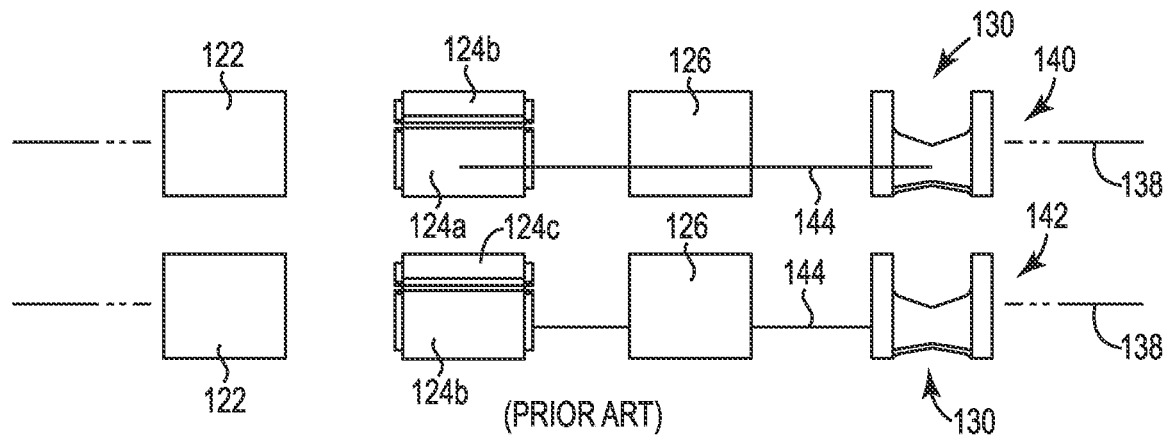
FIG. 6B is a radial view of the distal end of the known implantable lead of FIG. 6A with the implantable lead at first and second angular positions, according to one example.
Figure 6C:
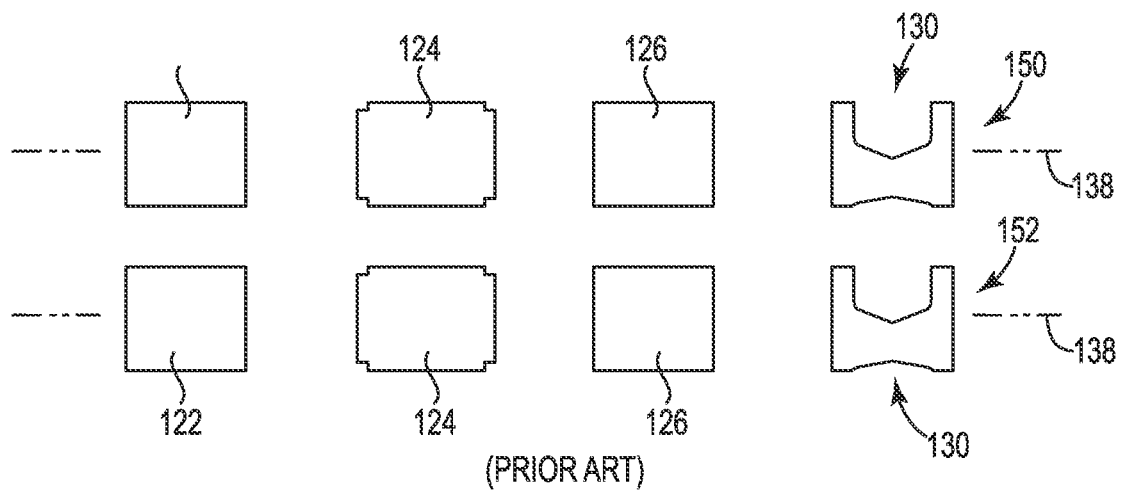
FIG. 6C generally illustrates radiographic images of the distal end of the known implantable lead of FIG. 6B with the implantable lead at first and second angular positions.

FIGS. 6A-6C illustrate the visible and radiographic appearance of a known fiducial marker 130 of a known implantable lead 120. FIG. 6A is a perspective view of lead 120, which includes electrodes 122, 124, and 126, with at least electrode 124 being segmented to form electrode segments 124a, 124b, and 124c. Lead 120 further includes a fiducial marker 130 having proximal and distal ends 132 and 134 connected by a central portion 136. Similar to that described above with regard to FIGS. 5A-5C, it is noted that the lead body of lead 120 is not shown for clarity of illustration. With reference to FIG. 6A, it is apparent that fiducial marker 130 is not asymmetrical about a longitudinal axis 138 when viewed from any radial direction thereof. For example, when viewed along a radius 139 of longitudinal axis 138, rather than being asymmetric, fiducial marker is symmetrical about longitudinal axis 138. It is noted that fiducial marker 130 will also be symmetrical about longitudinal axis 138 when viewed from the opposing radial direction. As a result, as illustrated below, fiducial marker 130 will not provide a unique radiographic silhouette from each radial direction.

FIG. 6B includes a first view 140 of lead 120 when from a given radial direction, where lead 120 is at a first angular orientation. FIG. 6B further includes a second view 142 from the same given radial direction, except that lead 120 is shown as having been rotated about longitudinal axis 138 by 180 degrees. In FIG. 5B, the line 144 is intended to illustrate that fiducial marker 130 is disposed such that central portion 136 is aligned with electrode segment 124a and faces the viewer in view 140, and faces away from the viewer in view 142.

FIG. 6C includes views 150 and 152 which represent radiographic images of lead 120 respectively corresponding to views 140 and 142 of FIG. 6B. As illustrated, the radiographic silhouette of fiducial marker 130 is the same in view 150 as in view 152. As such, in contrast to fiducial marker 70, in accordance with the present disclosure, based on the radiographic images 150 and 152, a practitioner is unable to ascertain the angular orientation of lead 120 based on a radiographic image of fiducial marker 130 from any radial direction, thereby requiring additional imaging and additional time in order to achieve a desired placement of lead 120.

In order to resolve imaging for lead 120, lead 120 may be rotated such that once the angle between the direction of viewing and the axis of the part departs from 90 degrees, orientation of the prior art becomes easier to distinguish. Such extra imaging is not needed, however, in conjunction with fiducial marker 70 in accordance with the present disclosure, because fiducial marker 70 provides added visual clarity due to the resolution of current radioscopic techniques, especially at small sizes (0.8 mm OD).

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof

What is claimed is:
1. A fiducial marker for use with an implantable lead, comprising:
a structure extending along and about a longitudinal axis, the structure having an asymmetrical shape about the longitudinal axis when viewed in any radial direction from the longitudinal axis so as to provide a unique radioscopic silhouette in any radial direction, the structure including a proximal portion, a distal portion, and a central portion extending between the proximal portion and the distal portion;
the proximal portion comprising a band having an internal circumference forming one end of the elongated opening;
the distal portion comprising a segment extending parallel to the longitudinal axis; and
the central portion comprising a helically-shaped element connected between the band and the segment.
2. The fiducial marker of claim 1, the proximal portion, distal portion, and central portion defining an elongated channel extending along the longitudinal axis, the elongated channel to receive an elongated portion of the implantable lead.
3. The fiducial marker of claim 2, the elongated channel having a circular cross-section.
4. The fiducial marker of claim 1, the helically-shaped element extending about at least a portion of the circumference of the elongated opening.
5. The fiducial marker of claim 1, where surfaces of the proximal, distal, and central portions facing the longitudinal axis define the circumference of the elongated opening.
6. The fiducial marker of claim 1, the fiducial marker comprising a metal.
7. An implantable lead comprising:
an elongated lead body extending along a longitudinal axis and having a proximal end and a distal end;
a plurality of electrodes disposed about a circumference of the lead body at the distal end and spaced apart from one another along the longitudinal axis; and
a fiducial marker disposed about at least a portion of the circumference of the lead body at the distal end, the fiducial marker disposed at a known position relative to the plurality of electrodes and having a structure with an asymmetrical shape about the longitudinal axis when viewed in any radial direction from the longitudinal axis so as to provide a unique radioscopic silhouette in any radial direction, the fiducial marker including a proximal portion, a distal portion, and a central portion extending between the proximal portion and the distal portion;
the proximal portion comprising a band;
the distal portion comprising a segment extending parallel to the longitudinal axis; and
the central portion comprising a helically-shaped element connected between the band and the segment.
8. The implantable lead of claim 7, including a conductor bundle extending along the longitudinal axis of the lead body, the conductor bundle including a conductor electrically connected to each of the electrodes of the plurality of electrodes.
9. The implantable lead of claim 8, the structure of the fiducial marker defining a perimeter of an elongated channel extending along the longitudinal axis, the elongated structure to receive the conductor bundle of the implantable lead, the band having an internal circumference forming one end of the elongated channel.
10. The implantable lead of claim 9, including a molded or reflowed insulating material forming an external surface of the elongated lead body, the molded or reflowed insulating material encasing the conductor bundle and separating the plurality of electrodes and the fiducial marker from one another, where surfaces the plurality of electrodes and the fiducial marker are flush with the molded or reflowed insulating material and form a portion of the external surface.

11. The implantable lead of claim 7, the distal end segment positioned at a known fixed position relative to the plurality of electrodes.

12. The implantable lead of claim 7, the helically-shaped element extending about at least a portion of the circumference of the elongated opening.

13. The implantable lead of claim 7, where inner surfaces of the proximal, distal, and central portions facing the longitudinal axis define the circumference of the elongated opening and engage a circumferential surface of the conductor bundle.

14. The implantable lead of claim 13, the inner surfaces of fiducial marker structure coated with an insulating material.

15. A fiducial marker for use with an implantable lead, the fiducial marker comprising:
   a proximal element;
   a distal element;
   a central element connected between the proximal and distal elements, the proximal, distal, and central elements extending along and about a longitudinal axis, the central element extending helically about the longitudinal axis between the proximal and distal elements and having an asymmetrical shape to give the fiducial marker a different radioscopic profile when viewed in each radial direction from the longitudinal axis; and wherein the proximal element comprises a band having an internal circumference, and the distal element comprises a linear segment extending parallel to the longitudinal axis.

16. The fiducial marker of claim 15, wherein surfaces of the proximal element, distal element, and central element facing the longitudinal axis define an elongated channel to receive an elongated portion of the implantable lead.

17. The fiducial marker of claim 16, wherein the elongated channel has a circular cross-section in a direction perpendicular to the longitudinal axis.

\* \* \* \* \*